United States Patent [19]
Kötzsch et al.

[11] 4,016,188
[45] Apr. 5, 1977

[54] PROCESS FOR THE PREPARATION OF LOW SILANES AND SILANE ESTERS

[75] Inventors: Hans-Joachim Kötzsch, Rheinfelden; Hans-Joachim Vahlensieck, Wehr, both of Germany

[73] Assignee: Dynamit Nobel Aktiengesellschaft, Troisdorf, Germany

[22] Filed: Mar. 10, 1975

[21] Appl. No.: 556,994

Related U.S. Application Data

[63] Continuation-in-part of Ser. No. 360,486, May 15, 1973, abandoned.

[30] Foreign Application Priority Data

May 30, 1972 Germany ..................... 2226265

[52] U.S. Cl. ............... 260/448.8 R; 260/448.2 P; 423/324; 423/325; 423/347
[51] Int. Cl.[2] ................. C07F 7/18; C01B 33/00; C01B 33/20; C01B 33/04
[58] Field of Search ............ 260/448.8 R, 448.2 P; 423/324, 325, 347

[56] References Cited

UNITED STATES PATENTS

| | | | |
|---|---|---|---|
| 2,626,273 | 1/1953 | Hunter et al. | 260/448.8 R |
| 2,627,451 | 3/1953 | Erickson et al. | 423/347 X |
| 2,735,861 | 2/1956 | Erickson et al. | 260/448.8 R |
| 3,105,086 | 9/1963 | Ryan | 260/448.8 R |
| 3,627,501 | 12/1971 | Kruger | 260/448.8 R X |

Primary Examiner—Paul F. Shaver
Attorney, Agent, or Firm—Burgess, Dinklage & Sprung

[57] ABSTRACT

A process for preparing monosilane and low silane esters thereof which comprises contacting a hydrogen silane ester of the formula $H_xSi(OR)_{4-x}$, wherein R represents an alkyl or alkoxyalkyl moiety and $x$ is 1, 2 or 3, with a catalyst of an element of the first group and/or the second or third main or secondary group of the periodic system or iron or manganese or and organic nitrogen compound under distillation conditions and recovering a product having the formula $H_{x+1}Si(OR)_{4-x-1}$ and/or a product of the formula $H_{x-1}Si(OR)_{4-x+1}$.

25 Claims, No Drawings

PROCESS FOR THE PREPARATION OF LOW SILANES AND SILANE ESTERS

CROSS REFERENCE TO RELATED APPLICATION

This is a continuation-in-part of application Ser. No. 360,486 filed May 15, 1973, now abandoned.

BACKGROUND OF THE INVENTION

This invention relates to the disproportionation of lower silane esters of the formula $H_xSI(OR)_{4-x}$ to obtain from such disproportionation a mixture of silane esters where the components of the mixture contain varying amounts of hydrogen and ester moieties. The present invention is also directed to a process for the preparation of monosilane and low silane esters by the catalytic disproportionation of hydrogen silane esters of the above formula.

DISCUSSION OF THE PRIOR ART

Hitherto it has been possible to obtain hydrogen silane esters of low silanes only with great difficulty. They form as by-products in the reaction of silicon with alcohols by the process of W. German Pat. No. 1,127,338. This process, however, is very expensive and does not result in pure products.

The direct esterification of dihydrogen dichlorosilane with alcohols to form the corresponding dihydrogen dialkoxy-silanes has not been achieved to this date. Hitherto such attempts have always led to the corresponding silicic acid orthoesters.

SUMMARY OF THE INVENTION

Broadly, this invention contemplates a process for preparing a compound of the formula $H_{x+1}Si(OR)_{4-x-1}$ or one of the formula $H_{x-1}Si(OR)_{4-x+1}$ wherein R is alkyl or alkylalkoxy and $x$ equals 1, 2 or 3 which comprises reacting a compound of the formula $H_xSi(OR)_{4-x}$ in the presence of a catalyst comprising an element of the first main group of the second or third main or secondary groups of the periodic system or iron or manganese or an organic nitrogen compound under distillation conditions, distilling over and recovering a product of the formula $H_{x+1}si(OR)_{4-x-1}$ and/or a product of the formula $H_{x-1}Si(OR)_{4-x+1}$.

The present invention can also be considered a process for disproportionating silicon esters of the formula $H_xSi(OR_{4-x}$ wherein R and $x$ have been previously ascribed significance by a process which comprises heating the same up to the boiling point of the desired hydrogen silan ester in the presence of a catalyst of the first main group or the second or third main or secondary groups of the periodic system or manganese or iron or an organic nitrogen compound, distilling over and recovering reaction products comprising a product of the formula $H_{x+1}Si(OR)_{4-x-1}$ and a product of the formula $H_{x-x}Si(OR)_{4-x+1}$. It has therefore been found that lower silane esters can be prepared from more esterified esters by a disproportionation process in which two moles of the higher silane ester are disproportionated to provide a mixture of a lower and a higher silane ester. For instance, when two moles of trialkoxysilane are disproportionated, there is provided one mole, on the stoichiometric basis, of didihydrogen dialkoxysilane and one mole of a tetraalkoxysilane. This is a true disproportionation reaction wherein one of the reaction products has more hydrogen atoms than the product disproportionated and the other of the reaction products contains less hydrogen. Similarly, one of the reaction products, the reaction product containing the greater number of hydrogen atoms, contains less alkoxy groups. By the same token, the compound containing less hydrogen atoms in the reactants contains more alkoxy groups in the final product.

The present invention is carried out by charging the silane ester into a vessel equipped with distillation equipment. The process is conducted at the temperature at which the first desired product distills over, i.e. at approximately the boiling point of the desired product. Thus, the product to be disproportionated is heated, together with catalyst and any solvent, initially up to about the boiling point of the desired compound of lowest boiling point. Generally speaking, it is heated up to a temperature between 10° and 0° C of the boiling point of such desired compound. After the compound distills over and is recovered by the usual distillation procedures, the reaction mixture is thereafter heated up to approximately the boiling point of the remaining reaction product. The remaining reaction product can be determined knowing the stoichiometry of the reaction. For instance, if a trialkoxysilane is disproportionated and the first component taken overhead and recovered is hydrogen silane, then it is known that the remaining reaction mixture comprises a substantial amount of a dialkoxysilane. Indeed, it must be remembered that the dialkoxysilane itself can undergo disproportionation to yield a mixture of product comprising trialkoxysilane and monoalkoxysilane, both of which can still further disproportionate. The temperature is maintained between 10° and 0° C of the boiling point of the product being removed until substantially all of the product has distilled overhead and been recovered. During this period of time the lower silane ester being disproportionated continuously reacts to form the disproportionation product being distilled off. Distillation is performed on the product as it is synthesized.

DESCRIPTION OF PREFERRED EMBODIMENTS

By this new process hydrogen silane esters are obtainable in great purity. It is advantageous that the process can be controlled so as to hydrogenate the silicon to any desired degree, with virtually quantitative yields. By means of the invention, one can, for example, disproportionate a trialkoxysilane if the formed dialkoxy dihydrogen silane is removed by distillation immediately after its formation and consequently cannot disproportionate any further. On the other hand, one can also allow the disproportionation reaction to continue further by not distilling the dialkoxysilane that is forming, so that one can obtain the monoalkoxysilane selectively and also virtually quantitatively by distilling it out as it forms.

The disproportionation reaction of the invention takes place in accordance with the following equation:

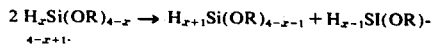

Without the presence of a catalyst, no reaction takes place. It has been found, however, that this reaction takes place virtually quantitatively in the presence of catalytic amounts of metals or metal compounds. It is surprising that, under the conditions of this process, the thermodynamically stable hydrogen silane is not immediately obtained, and that, instead, all intermediate degrees of hydrogenation can be obtained selectively. This is believed to be due to the catalyst employed.

The process of the invention is independent of temperature. The reaction takes place even at room temperature, and it can also be performed at the boiling points of the hydrogen silane esters that form. It is even possible to use a vacuum, especially in the production of hydrogen silane esters with higher boiling points.

The alkyl group of the ester component has up to 10 carbon atoms, preferably up to 4 carbon atoms. Basically, the reaction of the invention can be performed with hydrogen silane esters whose alkoxy group has up to 10 carbon atoms.

The starting product for the process of the invention is mainly hydrogen trialkoxysilanes which are obtained in a known manner through the reaction of trichlorosilane with the corresponding alcohols. Other hydrogen alkoxysilanes, however, may also be used as starting products, as for example, those which are obtained by the present process. In the reaction, the hydrogen alkoxysilane of the next higher degree of hydrogenation always forms first, together with the hydrogen alkoxysilane of the corresponding lower degree of hydrogenation. If the hydrogen alkoxysilane having the higher degree of hydrogenation, and hence the lower boiling point, is not removed by distillation as it forms, the alkoxysilanes of the next higher degree of hydrogenation form. The end products of the disproportionation reaction are monosilane and tetralkoxysilanes, respectively, depending upon to what extent the reaction is carried out.

As already stated above, any of the intermediate degrees of hydrogenation can be produced selectively. For example, hydrogentrimethoxysilane can be disproportionated selectively to dihydrogendimethoxysilane or trihydrogenmethoxysilane or monosilane, on the one hand, and tetramethoxysilane on the other. In like manner, dihydrogendimethoxysilane can serve for the production of trihydrogenmethoxysilane or monosilane on the one hand and hydrogentrimethoxysilane or tetramethoxysilane on the other. Likewise, trihydrogenmethoxysilane reacts to form monosilane on the one hand and dihydrogendimethyoxysilane, hydrogentrimethoxysilane and tetramethoxysilane on the other hand. Similarly, hydrogentriethyoxysilane for example, selectively forms dihydrogendiethoxysilane or trihydrogenethoxysilane or monosilane along with tetraethoxysilane. An additional example is hydrogentri-(2-methoxyethoxy)-silane, which can be disproportionated selectively to dihydrogendi-(2-methoxyethoxy)-silane or trihydrogen-(2-methoxyethoxy)-silane or monosilane, tetra-(2-methoxyethoxy)-silane being formed as a second product.

Catalysts which are useful in the process of the invention are metals or compounds of metals of the first main group as well as those of the second and third main groups and secondary groups of the periodic system, and also iron and manganese, or an organic compound containing bound nitrogen. By the "periodic system" there is meant the periodic table-short form shown in the *Encyclopedia of Chemical Technology* by Kirk-Othmer, Volume 8, page 96. The elements in a "main" group are those on the left of a column within a box and those in a "secondary" group are on the right. Some of these compounds are effective in quantities of as little as 0.001% by weight. In general, however, the catalyst is used in quatities of up to 2% by weight. The catalyst does not have to be soluble in the silane, and it can also act in dispersed or emulsified form.

Catalysts of the first main group of the periodic system are especially lithium in metallic form or lithium compounds, such as lithium oxide, lithium hydroxide, lithium carbonate, lithium alcoholates especially of $C_1$–$C_6$ alcohols and particularly $C_1$–$C_4$ alkanols, lithium phosphate, the lithium halides, etc. But other alkali metals, sodium, potassium, rubidium, and cesium, and compounds thereof such as sodium bicarbonate, potassium hydroxide, cesium oxide, sodium silicates, sodium borate, etc., have a strong catalytic effect.

Of the second main group of the periodic system, the preferred catalyst is magnesium, as metal or in the form of its organic or inorganic compounds, e.g., oxide, halide, chloride, carbonate, acetate, ethylate, acetylacetonate, etc. All of the other alkaline earth metals, however, such as calcium, strontium and barium, are catalytically active in accordance with the invention, both in metallic and in compound form, as oxides, for example, halides, hydroxides, carbonates, acetates, acetylacetonates, etc. Catalysts from the second secondary group are preferably elementary or chemically bound zinc or cadmium.

Of the third main group and secondary group, catalytically active elements are especially aluminum, lanthanum, cerium, thorium and uranium, in metallic form or in compounds. Iron is effective especially in finely granular metallic form, which is best produced in the reaction mixture by the hydrogen silane by reduction from iron compounds such as $FeSO_4$ or iron acetylacetonates, etc. Manganese, however, is catalytically active either as metal or in compounds such as $MnCl_2$, $MnCO_3$, manganese acetylacetonate, etc.

Catalytically active nitrogen-containing organic compounds are, for example, primary, secondary and tertiary amines, especially $C_1$–$C_8$ alkylamines such as triethylamine or tributylamine, or substituted or unsubstituted carboxylic acid amides, especially $C_1$–$C_8$ alkanoic acid amides such as urea, dimethylformamide or diethylformamide. The amides of the phosphoric acids, however, also show catalytic activity, such as hexamethylenephosphoric acid triamide, for example.

Heterocyclic nitrogen compounds can also be used as catalysts, examples being pyridine, quinoline, isoquinoline or piperidine.

The process of the invention is performed in a distillation column. The silane serving as the starting material is mixed in the sump with the catalyst, which may be in solid, suspended or water-free dissolved form. Then the mixture is boiled with refluxing until the boiling temperature of the desired lower-boiling disproportionation product is established at the top of the column. The reaction mixture is held at ± 2° C of the boiling point of the desired product. Then, by controlling the return ratio, the product in question is removed by distillation. Generally, the return ratio during distillation is between 1 and 100. The higher-boiling disproportionation product, however, remains in the distillation residue.

The hydrogen silane products prepared by this process are silanizing agents for glass and ceramic surfaces or other mineral substances. They are also suitable as catalyst components in the polymerization of substances with olefinic double bonds, and as specific reducing agents, for metals, for example.

Furthermore, the products of the process serve as purification stages in the production of transistor silicon of especially high purity. In particular, the hydrogen silane which is easily obtainable by this process leads to high-purity silicon having especially good semiconductor characteristics.

The esters of orthosilicic acid which are formed in the process of the invention are also valuable end products which can be used immediately, without further treatment, for zinc dust colors, for silicone rubber, or as a binding agent for mineral substances and for the preparation of investment molds for casting metal articles with smooth surfaces by the lost-wax process.

In order to more fully illustrate the invention and the manner of practicing the same, the following examples are presented:

EXAMPLE 1

In a distillation apparatus consisting of a sump having a capacity of 6 liters which can be heated by means of an internal heating coil through a thermostat, a column having a filling depth of 1.2 m and a diameter of 40 mm, filled with 3 × 3 mm porcelain, saddle-shaped packing bodies, and a nitrogen-flooded column head with receiver, 4 kilograms of pure trimethoxysilane are mixed in the sump with 2 grams of finely powdered magnesium acetylacetonate. The mixture is refluxed for about 30 minutes until a boiling point of 38° C is established. Then, with a return ratio of 12, the dimethoxysilane (B.P. 38° C) is distilled out in approximately 10 hours, the sump temperature rising from 84° C to 122° C. Dimethoxysilane forms in a yield of 1430 g (96%).

Then, after an intermediate run of about 100 grams which contains a small amount of dimethoxysilane and tetramethoxysilane plus some trimethoxysilane, tetramethoxysilane of a boiling point of 122° C is distilled in a yield of about 2400 g (approximately 95%). Both products are pure and can be used without further processing.

0.5 ml of the dimethoxysilane that was formed evolved 231 N ml (normal milliliters) of $H_2$ (236 N ml of $H_2$ is calculated for $C_2H_8O_2Si$ at $D._4^{20}$ 0.968).

| Elemental Analysis (molecular weight 92): | | | |
|---|---|---|---|
| | C | H | Si |
| Found | 26.4% | 8.5% | 20.2% |
| Calculated | 26.1% | 8.7% | 30.4% |

EXAMPLE 2

Four kg of triethoxysilane are mixed in the distillation apparatus described in Example 1 with 2 kg of hexamethylphosphoric acid triamide and refluxed for 1 hour until the temperature at the head of the column has established itself at 79° to 80° C. Then with a return ratio of 20, the diethoxysilane (B.P. 79° to 80° C) is distilled out in approximately 24 hours, the sump temperature rising from 132° C to about 168° C. Diethoxysilane forms in a yield of 1410 grams (96%).

Then, after an intermediate distillation run of about 100 g containing a small amount of diethoxysilane and tetraethoxysilane plus a little triethoxysilane, tetraethoxysilane with a boiling point of 168° C is distilled over in a yield of 2440 g (96%).

Both products are pure and can be used directly without further processing.

0.5 ml of diethoxysilane evolved 154 N ml $H_2$ with 25% potash lye (156 N ml $H_2$ calculated for $C_4H_{12}O_2Si$ at $D._4^{20}$ 0.832).

| Elemental Analysis: (molecular weight 120): | | | |
|---|---|---|---|
| | C | H | Si |
| Found | 40.2% | 9.7% | 23.0% |
| Calculated | 40.0% | 10.0% | 23.3% |

EXAMPLE 3

Four kg of tri-(2-methoxyethoxy)-silane is mixed in the distillation apparatus described in Example 1 with 2 g of iron (II)-acetylacetonate and refluxed for 8 hours in a vacuum of 4 Torr until a temperature of 58° to 60° C has been established at the top of the column, the contents of the sump turning black due to the reduction of the iron(II) acetylacetonate to metallic iron. Then, the di-(2-methoxyethoxy)-silane (B.P.$_4$ 58° to 60° C, $n_D^{20}$ <1.3) is distilled out, the sump temperature rising from about 96° C to about 140° C. Di-(2-methoxyethoxy)-silane forms in a yield of 1320 g (93%).

After an intermediate distillation run of about 200 g containing a small amount of di-(2-methoxyethoxy)-silane and tetra-(2-methoxyethoxy)-silane plus some tri-(2-methoxyethoxy)-silane, tetra-(2-methoxyethoxy)-silane with a boiling point of 141° to 144° C at 4 Torr is distilled out in a yield of 2330 g (91%).

Both products were pure and directly usable without further processing.

One ml of di-(2-methoxyethoxy)-silane with 25% potash lye evolved 252 N ml of $H_2$ (249 N ml $H_2$ calculated for $C_6H_{16}O_4$ at $D._4^{20}$ 0.997).

| Elemental Analysis (molecular weight 180): | | | |
|---|---|---|---|
| | C | H | Si |
| Found | 40.3% | 8.5% | 15.3% |
| Calculated | 40.0% | 8.9% | 15.6% |

EXAMPLE 4

Similar to Example 2: 4 kg of triethoxysilane with 2 g of aluminum acetylacetonate yields 685 g (47%) diethoxysilane, 1100 g tetraethoxysilane and 2085 g unchanged triethoxysilane.

EXAMPLE 5

Similar to Example 1: 4 kg of trimethoxysilane with 2 g of zinc acetylacetonate yields 1290 g (86%) dimethoxysilane, 2060 g tetramethoxysilane and about 500 g of unchanged trimethoxysilane.

EXAMPLE 6

Four kg of double-distilled triethoxysilane was refluxed with 2 g of sodium tert.-butylate for 12 hours until the head of the column had reached a boiling temperature of 168° C. During this period hydrogen silane was detected by gas chromatography in the exhaust from the nitrogen flooding. After the head temperature had reached 168° C, approximately 3700 g of tetraethoxysilane was distilled out, which was free of triethoxysilane. From the difference of yield and weight it was calculated that about 200 g of hydrogen silane had formed, which corresponds to the theoretical amount.

EXAMPLE 7

Four kg of double-distilled diethoxysilane was refluxed with 2 g of lithium chloride for 10 hours until the head of the column had reached a boiling temperature of 168° C. During this period hydrogen silane was detected by gas chromatography in the exhaust from the nitrogen flooding. After the head temperature had reached 168° C, about 3400 g of tetraethoxysilane as distilled out, which was free of triethoxysilane. From the difference of yield and weight it was calculated that about 500 g of hydrogen silane had been formed, and this corresponds to the theoretical amount.

EXAMPLES 8 to 16

In the same manner as described in Example 1, 4 kg of trimethoxisilane are heated with 2 g of one of the following compounds: acetylacetonate of manganese or cerium, N,N,-dimethylamino-acetonitrile or the salts of zinc, calcium or magnesium, named in table 1. When the temperature on the top of the distillation column reached the boiling point of dimethoxisilane, this product is distilled off with a return ratio of 15, whereby the sump temperature raises to 125° C within the indicated time. The results are shown in table 1.

EXAMPLES 17 to 25

Similar to Example 2, 4 kg of tri-ethoxisilane, mixed with the compounds named in table 2, are heated within 60 minutes to such a sump temperature that at the head of the column the temperature is 79° to 80° C. With a return ratio of 20, di-ethoxisilane is then distilled off during 10 hours. The resulting yields of diethoxisilane are shown in table 2.

Table 1

| | Disproportionation of trimethoxisilane to dimethoxisilane | | |
|---|---|---|---|
| Example | catalyst | distillation time ($\mu$) | yield |
| 8 | Cer(III)tris-acetylacetonate | 12 | 95% |
| 9 | Manganese (III) tris-acetylacetonate | 14 | 96% |
| 10 | zinc-oxalate | 36 | 74% |
| 11 | zinc sulfate | 40 | 70% |
| 12 | magnesium acetate | 24 | 66% |
| 13 | magnesium carbonate | 24 | 82% |
| 14 | calcium oxalate | 24 | 89% |
| 15 | calcium carbonate | 24 | 92% |
| 16 | N,N-dimethylamino-acetonitrile | 12 | 96 |

Table 2

| | Disproportion of triethoxisilane to diethoxisilane and tetraethoxisilane | |
|---|---|---|
| Example | catalyst employed | yield of diethoxisilane |
| 17 | Fe SO$_4$ | 22% |
| 18 | Fe (II) oxalate | 29% |
| 19 | Al-oxalate | 11% |
| 20 | Ce$_2$(SO$_4$)$_3$ | 86% |
| 21 | Mn SO$_4$ | 91% |
| 22 | tributylamine | 78% |
| 23 | allylamine | 47% |
| 24 | acetamide | 29% |
| 25 | dimethylformamide | 45% |

What is claimed is:

1. In a process for preparing a compound of the formula $H_{x+1}Si(OR)_{4-x-1}$ or one of the formula $H_{x-1}Si(OR)_{4-x+1}$ wherein R is alkyl or alkoxyalkyl wherein the alkyl portion has up to 10 carbon atoms and $x$ equals 1, 2 or 3 by reacting a compound of the formula $H_xSi(OR)_{4-x}$ in the presence of a catalyst under distillation conditions, distilling over and recovering a product of the formula $H_{x+1}Si(OR)_{4-x-1}$ or a product of the formula $H_{x-1}Si(OR)_{4-x+1}$, the improvement which comprises utilizing as the catalyst an oxide, halide, chloride, carbonate, acetate, ethylate or acetyl acetonate of zinc, cadmium, magnesium, calcium, strontium or barium, metallic zinc, metallic cadmium, metallic calcium, metallic magnesium, metallic strontium or metallic barium or metallic manganese or manganese chloride, manganese carbonate or zinc, aluminum or manganese acetylacetonate or an organic nitrogen compound selected from the group consisting of primary $C_1$–$C_8$ alkylamines, secondary $C_1$–$C_8$ alkylamines, tertiary $C_1$–$C_8$ alkylamines, substituted carboxylic acid amides of $C_1$–$C_8$ alkanoic acid amides, amides of phosphoric acid, pyridine, quinoline, isoquinoline and piperidine.

2. A process according to claim 1 wherein the catalyst is in the form of a compound.

3. A process according to claim 1 wherein the catalyst is an element in metallic form.

4. In a process for preparing a compound of the formula $H_{x+1}Si(OR)_{4-x-1}$ or one of the formula $H_{x-1}Si(OR)_{4-x+1}$ wherein R is alkyl or alkoxy alkyl wherein the alkyl portion has up to 10 carbon atoms and $x$ equals 1, 2 or 3 by reacting a compound of the formula $H_xSi(OR)_{4-x}$ in the presence of a catalyst under distillation conditions, distilling over and recovering a product of the formula $H_{x+1}Si(OR)_{4-x-1}$ or a product of the formula $H_{x-1}Si(OR)_{4-x+1}$ which comprises utilizing as the catalyst a catalyst selected from the group consisting of lithium hydroxide, lithium oxide, lithium carbonate, lithium phosphate, lithium halide, sodium bicarbonate, cesium oxide, sodium silicate, sodium borate, magnesium oxide, magnesium halide, magnesium carbonate, magnesium acetate, magnesium ethylate, magnesium acetylacetonate, metallic magnesium, metallic calcium, metallic strontium, metallic barium, an oxide, halide, hydroxide, carbonate, acetate or acetylacetonate of calcium, strontium or barium, metallic aluminum, metallic lanthanum, metallic cerium, metallic thorium, metallic uranium, metallic iron, FeSO$_4$, iron acetylacetonate, manganese chloride, manganese metal, manganese carbonate, manganese acetylacetonate, manganese sulfate, aluminum acetylacetonate, zinc acetylacetonate, primary $C_1$–$C_8$ alkyl amines, secondary $C_1$–$C_8$ alkyl amines, tertiary $C_1$–$C_8$ alkyl amines, a $C_1$–$C_8$ alkanoic acid amine, an amide of phosphoric acid, pyridine, quinoline, isoquinoline and piperidine.

5. A process according to claim 4 wherein the catalyst is a $C_1$–$C_8$ alkyl amine a phosphoric acid amide or a $C_1$–$C_8$ alkanoic acid amide, said amine or amide is a composition selected from the group consisting of urea, dimethylformamide, diethylformamide and hexamethylene phosphoric acid triamide.

6. A process according to claim 1 wherein the catalyst is present in the reaction mixture in the form of a solid.

7. A process according to claim 1 wherein the catalyst is present in the reaction mixture in the form of a suspension.

8. A process according to claim 1 wherein the catalyst is present in a water-free dissolved form.

9. A process according to claim 1 wherein the reaction mixture is held at a temperature of between 10° and 0° C from the boiling point during distillative removal of the desired reaction product.

10. A process according to claim 1 wherein after said compound having the formula $H_xSi(OR)_{4-x}$ or $H_{x+1}Si(OR)_{4-x-1}$ or $H_{x-1}Si(OR)_{4-x+1}$ is removed, the reaction mixture is heated up to a higher temperature at which point a compound of the formula $H_{x+1}Si(OR)_{4-x-1}$ or $H_{x-1}Si(OR)_{4-x+1}$ is removed by distillation.

11. A process according to claim 1 wherein the compound reacted is a trialkoxysilane.

12. A process according to claim 1 wherein R is an alkyl group of up to 10 carbon atoms or an alkyl alkoxy group having up to 10 carbon atoms on the alkoxy group and up to 10 carbon atoms on the alkyl group.

13. A process according to claim 4 wherein the catalyst is magnesium acetylacetonate.

14. A process according to claim 4 wherein the catalyst is hexamethyl phosphoric acid triamide.

15. A process according to claim 4 wherein the catalyst is iron(II)-acetylacetonate.

16. A process according to claim 4 wherein the catalyst is aluminum acetylacetonate.

17. A process according to claim 4 wherein the catalyst is zinc acetylacetonate.

18. A process according to claim 1 wherein the compound reacted is trimethoxysilane.

19. A process according to claim 1 wherein the compound reacted is triethoxysilane.

20. A process according to claim 1 wherein the compound reacted is di-(2-methoxyethoxy)-silane.

21. A process according to claim 1 wherein the distillation is carried out such that the return ratio is between 1 and 100.

22. A process according to claim 4 wherein the catalyst is selected from the group consisting of magnesium oxide, magnesium halide, magnesium carbonate, magnesium acetate, magnesium ethylate, magnesium acetylacetonate, metallic magnesium, metallic calcium, metallic strontium, metallic barium, an oxide, halide, hydroxide, carbonate, acetate or acetylacetonate of calcium, strontium or barium metallic aluminum, metallic lanthanum, metallic cerium, metallic thorium, metallic uranium, metallic iron, $FeSO_4$, iron acetylacetonate. primary $C_1$–$C_8$ alkyl amines, secondary $C_1$–$C_8$ alkyl amines, tertiary $C_1$–$C_8$ alkyl amines, a $C_1$–$C_8$alkanoic acid amide, pyridine, quinoline, isoquinoline and piperidine.

23. A process according to claim 4 wherein the catalyst is lithium chloride.

24. A process according to claim 4 wherein the catalyst is magnesium chloride.

25. A process according to claim 22 wherein the catalyst is selected from the group consisting of magnesium oxide, magnesium halide, magnesium carbonate, magnesium acetate, magnesium ethylate, magnesium acetylacetonate, metallic magnesium, metallic calcium, metallic strontium, metallic barium, an oxide, hydroxide, carbonate, acetate or acetylacetonate of calcium, strontium or barium, metallic aluminum, metallic lanthanum, metallic cerium, metallic thorium, metallic uranium, metallic iron, $FeSO_4$, iron acetylacetonate, primary $C_1$–$C_8$ alkyl amines, secondary $C_1$–$C_8$ alkyl amines, tertiary $C_1$–$C_8$ alkyl amines, a $C_1$–$C_8$ alkanoic acid amide, pyridine, quinoline, isoquinoline and piperidine.

* * * * *

UNITED STATES PATENT AND TRADEMARK OFFICE
CERTIFICATE OF CORRECTION

PATENT NO. : 4,016,188
DATED : April 5, 1977
INVENTOR(S) : Hans-Joachim Kötzsch et al.

It is certified that error appears in the above-identified patent and that said Letters Patent are hereby corrected as shown below:

Column 1, line 48, change "$(OR_{4-x}$" to -- $(OR)_{4-x}$ --;

line 57, change "$H_{x-x}$" to -- $H_{x-1}$ --.

Column 8, line 54, after "alkyl amine" insert -- , -- (comma).

Signed and Sealed this

Twenty-eighth Day of June 1977

[SEAL]

Attest:

RUTH C. MASON
*Attesting Officer*

C. MARSHALL DANN
*Commissioner of Patents and Trademarks*